US00PP26272P2

(12) United States Plant Patent
Westhoff

(10) Patent No.: US PP26,272 P2
(45) Date of Patent: Dec. 22, 2015

(54) ***CALIBRACHOA* PLANT NAMED 'WESCACANDY'**

(50) Latin Name: ***Calibrachoa* sp.**
Varietal Denomination: Wescacandy

(71) Applicant: Heinrich Westhoff, Sudlohn (DE)

(72) Inventor: Heinrich Westhoff, Sudlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 112 days.

(21) Appl. No.: 14/120,009

(22) Filed: Apr. 15, 2014

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — June Hwu

(57) ABSTRACT

A new and distinct cultivar of *Calibrachoa* plant named 'Wescacandy', characterized by its compact, semi-upright and mounding growth habit; moderately vigorous growth habit; numerous small-sized mottled red purple and yellow-colored flowers with recurved flower petals; and good garden performance.

1 Drawing Sheet

Botanical designation: *Calibrachoa* sp.
Cultivar denomination: 'WESCACANDY'.

BACKGROUND OF THE INVENTION

The present invention relates to a new and distinct cultivar of *Calibrachoa* plant, botanically known as *Calibrachoa* sp. and hereinafter referred to by the name 'Wescacandy'.

The new *Calibrachoa* plant is a product of a planned breeding program conducted by the Inventor in Südlohn, Germany. The objective of the breeding program is to create new compact *Calibrachoa* plants with uniform plant habit and numerous attractive flowers.

The new *Calibrachoa* plant is a naturally-occurring whole plant mutation of *Calibrachoa* sp. 'USCAL91001', disclosed in U.S. Plant Pat. No. 23,232. The new *Calibrachoa* plant was discovered and selected by the Inventor as a single flowering plant from within a population of plants of 'USCAL91001' in a controlled greenhouse environment in Südlohn, Germany in April, 2013.

Asexual reproduction of the new *Calibrachoa* plant by vegetative cuttings in a controlled environment in Südlohn, Germany since April, 2013 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Wescacandy'. These characteristics in combination distinguish 'Wescacandy' as a new and distinct *Calibrachoa* plant:

1. Compact, semi-upright and mounding growth habit.
2. Moderately vigorous growth habit.

3. Numerous small-sized mottled red purple and yellow-colored flowers with recurved flower petals.
4. Good garden performance.

Plants of the new *Calibrachoa* can be compared to plants of the mutation parent, 'USCAL91001'. Plants of the new *Calibrachoa* differ primarily from plants of 'USCAL91001' in the following characteristics:

1. Plants of the new *Calibrachoa* have smaller flower buds and flowers than plants of 'USCAL91001'.
2. Flower petals of plants of the new *Calibrachoa* are recurved whereas flower petals of plants of 'USCAL91001' are flat.
3. Plants of the new *Calibrachoa* and 'USCAL91001' differ in flower color as plants of 'USCAL91001' have red purple-colored flowers with a distinct and narrow yellow-colored star pattern.

Plants of the new *Calibrachoa* can be compared to plants of the *Calibrachoa* sp. 'Wesviolet', disclosed in U.S. Plant Pat. No. 12,584. In side-by-side comparisons conducted in Südlohn, Germany, plants of the new *Calibrachoa* differed from plants of 'Wesviolet' in the following characteristics:

1. Plants of the new *Calibrachoa* were more compact than and not as vigorous as plants of 'Wesviolet'.
2. Plants of the new *Calibrachoa* had shorter and thicker lateral stems than plants of 'Wesviolet'.
3. Plants of the new *Calibrachoa* had larger leaves than plants of 'Wesviolet'.
4. Plants of the new *Calibrachoa* had smaller flower buds and flowers than plants of 'Wesviolet'.
5. Plants of the new *Calibrachoa* and 'Wesviolet' differed in flower color as plants of 'Wesviolet' had solid violet-colored flowers.

BRIEF DESCRIPTION OF THE PHOTOGRAPH

The accompanying colored photograph illustrates the overall appearance of the new *Calibrachoa* plant showing the colors as true as it is reasonably possible to obtain in colored reproductions of this type. Colors in the photograph may differ slightly from the color values cited in the detailed botanical description which accurately describe the colors of the new *Calibrachoa* plant.

The photograph comprises a side perspective view of a typical flowering plant of 'Wescacandy' grown in a container.

DETAILED BOTANICAL DESCRIPTION

The aforementioned photograph and following observations, measurements and values describe plants grown in 12-cm containers in Südlohn, Germany, under typical commercial cultural practices during the spring in a glass-covered greenhouse with day temperatures ranging from 20° C. to 25° C., night temperatures ranging from 16° C. to 18° C. and light levels ranging from 3 to 50 klux. Plants were pinched one time about four weeks after planting and plants were 15 weeks old when the photograph and description were taken. In the following description, color references are made to The Royal Horticultural Society Colour Chart, 2001 Edition, except where general terms of ordinary dictionary significance are used.

Botanical classification: *Calibrachoa* sp. 'Wescacandy'.

Parentage: Naturally-occurring whole plant mutation of *Calibrachoa* sp. 'USCAL91001', disclosed in U.S. Plant Pat. No. 23,232.

Propagation:

*Type.*—By vegetative cuttings.

*Time to initiate roots, summer.*—About three to four weeks at temperatures about 18° C. to 20° C.

*Time to initiate roots, winter.*—About 3.5 to four weeks at temperatures about 18° C. to 20° C.

*Time to produce a rooted young plant, summer.*—About four to five weeks at temperatures about 18° C. to 20° C.

*Time to produce a rooted young plant, winter.*—About five to six weeks at temperatures about 18° C. to 20° C.

*Root description.*—Fibrous, medium in thickness; color, close to 158A.

*Rooting habit.*—Freely branching; moderately dense to dense.

Plant description:

*Plant and growth habit.*—Compact, semi-upright to mounding growth habit; freely branching habit with lateral branches potentially developing at every node; moderately vigorous growth habit.

*Plant height.*—About 15 cm to 20 cm.

*Plant diameter.*—About 58.5 cm.

Lateral branch description:

*Length.*—About 18 cm.

*Diameter.*—About 2.5 mm.

*Internode length.*—About 1.25 cm.

*Strength.*—Strong; flexible.

*Aspect.*—Initially upright to outwardly spreading.

*Texture.*—Pubescent.

*Color.*—Close to 146C.

Leaf description:

*Arrangement.*—Alternate, simple; sessile.

*Length.*—About 2.5 cm.

*Width.*—About 1.25 cm to 1.5 cm.

*Shape.*—Ovate.

*Apex.*—Obtuse.

*Base.*—Attenuate.

*Margin.*—Entire.

*Texture, upper and lower surfaces.*—Pubescent.

*Venation pattern.*—Pinnate; arcuate.

*Color.*—Developing leaves, upper surface: Close to 146A. Developing leaves, lower surface: Close to 146B. Fully expanded leaves, upper surface: Close to 147A; venation, slightly lighter than 147A. Fully expanded leaves, lower surface: Close to 147B; venation, slightly lighter than 147B.

Flower description:

*Flower arrangement and habit.*—Single salverform flowers arising from leaf axils; freely flowering habit with usually about six to ten flowers developing per lateral branch; flowers face mostly outwardly.

*Fragrance.*—None detected.

*Natural flowering season.*—Plants flower continuously from April to October in Germany.

*Flower longevity.*—Individual flowers last about five to seven days on the plant; flowers not persistent.

*Flower diameter.*—About 3 cm to 3.6 cm.

*Flower length (height).*—About 3.6 cm.

*Flower throat diameter.*—About 7.5 mm to 10 mm.

*Flower tube diameter, base.*—About 4 mm.

*Flower tube length.*—About 1.8 cm.

*Flower buds.*—Shape: Oblong. Length: About 1.8 cm. Diameter: About 4 mm. Color: Close to 151C; midsection and towards the apex, close to 16A to 16B; venation, close to 200A.

*Corolla.*—Arrangement: Five petals fused at the base and opening into a flared trumpet. Petal length from throat: About 2 cm to 2.3 cm. Petal lobe width: About 1.3 cm. Petal shape: Broadly obovate. Petal apex: Emarginate. Petal margin: Entire; recurved. Petal texture, upper and lower surfaces: Smooth, glabrous; satiny to dull. Color: Petal lobe, when opening, upper surface: Centers, close to 60B; along margins, close to 9B to 9C. Petal lobe, when opening, lower surface: Centers, close to 60C to 60D; along margins, close to 9C to 9D. Petal lobe, fully opened, upper surface: Centers, close to 61B to 61C with random spots, close to 9C; along margins, close to 9B to 9C; with development, colors becoming closer to N79C and 9D. Petal lobe, fully opened, lower surface: Centers, close to 63B; along margins, close to 9D; with development, center color becoming closer to N79D. Throat: Close to 163B; venation, close to 200D. Tube: Close to 151C; venation, close to 200A.

*Calyx.*—Arrangement: One star-shaped calyx tube with five sepals fused at the base per flower. Sepal length: About 1 cm. Sepal width: About 2.5 mm. Sepal shape: Lanceolate. Sepal apex: Obtuse. Sepal margin: Entire. Sepal texture, upper and lower surfaces: Smooth, glabrous; dull. Color, upper and lower surfaces: Close to 146A.

*Peduncles.*—Length: About 1.5 cm to 2 cm. Diameter: About 1.3 mm. Strength: Moderately strong; flexible. Texture: Pubescent. Color: Close to 144A.

*Reproductive organs.*—Stamens: Quantity/arrangement: About five per flower. Filament length: About 1 cm to 1.25 cm. Filament color: Close to 145C. Anther shape: Ovate, four-parted. Anther length: About 2.5 mm. Anther width: About 1.25 mm. Anther color: Close to 8B. Pollen amount: Scarce. Pollen color: Close to 13B. Pistils: Quantity: One per flower. Pistil length: About 1 cm. Style length: About 9 mm. Style color: Close to 144C to 144D. Stigma shape: Ovate. Stigma color: Close to 144A. Ovary color: Close to 144C. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 8° C. to about 28° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'Wescacandy' as illustrated and described.

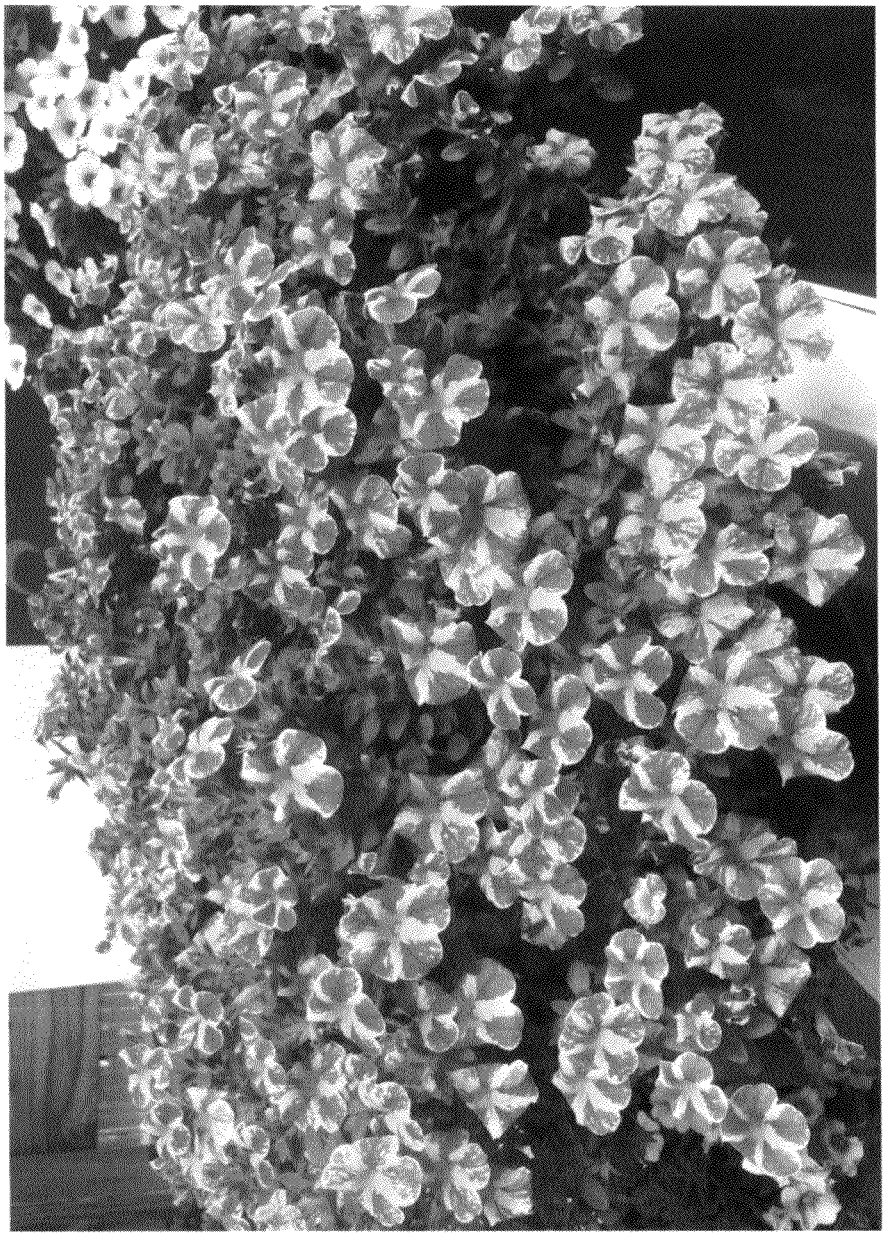

* * * * *